(12) United States Patent
Stout et al.

(10) Patent No.: US 10,413,595 B2
(45) Date of Patent: Sep. 17, 2019

(54) COMPOSITION AND METHODS FOR TREATING ISCHEMIC WOUNDS AND INFLAMMATORY CONDITIONS

(71) Applicant: Southwest Technologies, Inc., North Kansas City, MO (US)

(72) Inventors: Edward I. Stout, North Kansas City, MO (US); Chandan Sen, Columbus, OH (US)

(73) Assignee: Southwest Technologies, Inc., North Kansas City, MO (US)

( * ) Notice: Subject to any disclaimer, the term of this patent is extended or adjusted under 35 U.S.C. 154(b) by 0 days.

(21) Appl. No.: 15/540,661

(22) PCT Filed: Dec. 30, 2015

(86) PCT No.: PCT/US2015/068147
§ 371 (c)(1),
(2) Date: Jun. 29, 2017

(87) PCT Pub. No.: WO2016/109722
PCT Pub. Date: Jul. 7, 2016

(65) Prior Publication Data
US 2018/0000905 A1 Jan. 4, 2018

Related U.S. Application Data

(60) Provisional application No. 62/097,734, filed on Dec. 30, 2014.

(51) Int. Cl.
| | |
|---|---|
| *A61K 38/39* | (2006.01) |
| *A61K 38/42* | (2006.01) |
| *A61K 38/51* | (2006.01) |
| *A61L 26/00* | (2006.01) |

(52) U.S. Cl.
CPC ............ *A61K 38/39* (2013.01); *A61K 38/42* (2013.01); *A61K 38/51* (2013.01); *A61L 26/008* (2013.01); *A61L 26/0033* (2013.01); *A61L 2400/06* (2013.01); *C12Y 402/01001* (2013.01)

(58) Field of Classification Search
None
See application file for complete search history.

(56) References Cited

U.S. PATENT DOCUMENTS

| | | |
|---|---|---|
| 3,296,094 A | 1/1967 | Theodore |
| 4,344,967 A | 8/1982 | Easton et al. |
| 4,426,443 A | 1/1984 | Shank |
| 6,136,341 A | 10/2000 | Petito |
| 2003/0008830 A1 | 1/2003 | Prozillo |
| 2004/0224384 A1 | 11/2004 | Ishaq |
| 2006/0183680 A1 | 8/2006 | Tabata et al. |
| 2010/0173868 A1 | 7/2010 | Petito et al. |
| 2011/0269667 A1 | 11/2011 | Shoseyov et al. |
| 2012/0141575 A1* | 6/2012 | Kassner ............... A61K 38/39 424/443 |
| 2015/0216947 A1 | 8/2015 | Petito |

FOREIGN PATENT DOCUMENTS

| | | |
|---|---|---|
| WO | 2002053064 | 7/2002 |
| WO | 2014013027 | 1/2014 |

OTHER PUBLICATIONS

Elgharably et al. ("A modified collagen gel enhances healing outcome in a preclinical swine model of excisional wounds," Wound Repair and Regeneration, 2013, 21, pp. 473-481) (Year: 2013).*
Elgharably et al. ("A modified collagen gel dressing promotes angiogenesis in a preclinical swine model of chronic ischemic wounds," Wound Repair and Regeneration, 2014, 22, pp. 720-729) (Year: 2014).*
StimulenTM Collagen Powder, downloaded from www.woundsource.com (Year: 2018).*
StimulenTM, downloaded from www.elastogel.com (Year: 2018).*
StimulenTM Collagen, downloaded from fda.gov (Year: 2018).*
Elgharably, et al., "A Modified Collagen Gel Dressing Promotes Angiogenesis in a Pre-Clinical Swine Model of Chronic Ischemic Wounds", Wound Repair Regen., Nov.-Dec. 2014, vol. 22, issue 6, pp. 720-729.
Elder, et al., "Local Care of Diabetic Foot Ulcers: Assessment, Dressings, and Topical Treatments", The Diabetic Foot, Apr. 10, 2012, pp. 289-306 (abstract attached).
Gomez-Guillen, et al., "Functional and Bioactive Properties of Collagen and Gelatin From Alternative Sources: A Review", Food Hydrocolloids, Dec. 2011, vol. 25, issue 8, pp. 1813-1827.
International Search Report and Written Opinion in related PCT Application Serial No. PCT/US2015/068147, dated Mar. 7, 2016, 10 pages.
Elgharably, et al., "A Modified Collagen Gel Enhances Healing Outcome in a Pre-Clinical Swine Model of Excisional Wounds", Wound Repair Regen, May 2013, vol. 21, issue 3, pp. 473-481.

* cited by examiner

*Primary Examiner* — Christina Bradley
(74) *Attorney, Agent, or Firm* — Hovey Williams LLP

(57) ABSTRACT

Methods, compositions, and treatment protocols for treating ischemic wounds and inflammatory conditions in a patient. The treatment protocols comprise or consist of using a modified collagen gel (MCG) to promote healing of ischemic wounds and reduce inflammation at the wound site and in other inflammatory conditions. The modified collagen gel comprises generally a dispersion of collagens in an aqueous matrix comprising water and glycerine, where the amount of Type I collagen is greater than the amount of Type II and Type III collagens in the gel.

8 Claims, 17 Drawing Sheets
(9 of 17 Drawing Sheet(s) Filed in Color)

COMPOSITION AND METHODS FOR TREATING ISCHEMIC WOUNDS AND INFLAMMATORY CONDITIONS

CROSS-REFERENCE TO RELATED APPLICATIONS

The present application is the National Stage of International Patent Application No. PCT/US2015/068147, filed Dec. 30, 2015, which claims the priority benefit of U.S. Provisional Patent Application Ser. No. 62/097,734, filed Dec. 30, 2014, entitled Composition and Methods for Treating Ischemic Wounds and Inflammatory Conditions, each of which is incorporated by reference in its entirety herein.

BACKGROUND OF THE INVENTION

Field of the Invention

The present invention relates to compositions, methods, and treatment protocols for treating ischemic wounds and inflammatory conditions using a modified collagen gel.

Description of Related Art

Chronic wounds are rarely seen in individuals who are otherwise healthy. In the United States, chronic wounds affect over 6.5 million patients. The burden is also rapidly growing due to increasing healthcare costs, an aging population, and a sharp rise in the incidence of diabetes and obesity worldwide. With the cost of chronic wound care sharply rising, efforts are underway to find simple and inexpensive solutions that may be applied to a broad group of affected people. Ischemia is caused by limited blood supply to the wound site causing a shortage of oxygen and other blood-borne products required by the tissue to pay for the increased metabolic cost of healing. Peripheral vascular disease or disruption is a common cause of ischemia that may also be viewed as anemia localized to the wound site. Individuals with poor peripheral circulation are at high risk for developing ischemic wounds. Other medical conditions also associated with ischemic wounds are diabetes mellitus, renal failure, hypertension, lymphedema, inflammatory diseases such as vasculitis or lupus, and current or past tobacco use.

SUMMARY OF THE INVENTION

The present invention is broadly concerned with methods of treating an ischemic wound in a patient, where the patient has an ischemic wound site. The methods generally comprise (or consist of) applying a therapeutically effective amount of a modified collagen gel (MCG) composition to the ischemic wound site to yield a treated ischemic wound site. The gel is applied for a therapeutically effective period of time such that the modified collagen gel promotes healing of the treated ischemic wound site. In general, the modified collagen gel comprises (consists essentially or even consists of) modified collagen of long and short polypeptides, dispersed in an aqueous matrix comprising water and glycerine. Preferably, the modified collagen is a hydrolyzed bovine collagen. The modified collagen gel comprises each of Type I, Type II, and Type III collagens, but is primarily Type I and Type III, with Type I being the most abundant. The modified collagen gel comprises additional proteins, including hemoglobin (both alpha and beta subunits), and carbonic anhydrase 2.

The invention is also concerned with use of a modified collagen gel composition comprising a dispersion of about 52% by weight hydrolyzed bovine collagen, dispersed in an aqueous matrix comprising water and glycerine in the treatment of an ischemic wound. Preferably, the modified collagen gel comprises a plurality of proteins characterized according to Table 1 below.

Also described herein are methods of treating an inflammatory condition in a patient suffering from the inflammatory condition. The methods generally comprise (or consist of) administering a therapeutically effective amount of a modified collagen gel composition to the patient, such as to the location of inflammation in the patient. The modified collagen gel is administered for a therapeutically effective period of time, such that the modified collagen gel reduces the severity of the inflammatory condition in the patient. Administration can include topical application of the modified collagen gel to a site of dermal inflammation (for example), as well as injection of the modified collagen gel.

The invention is also concerned with use of a modified collagen gel composition comprising a dispersion of about 52% by weight hydrolyzed bovine collagen, dispersed in an aqueous matrix comprising water and glycerine in the treatment of an inflammatory condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
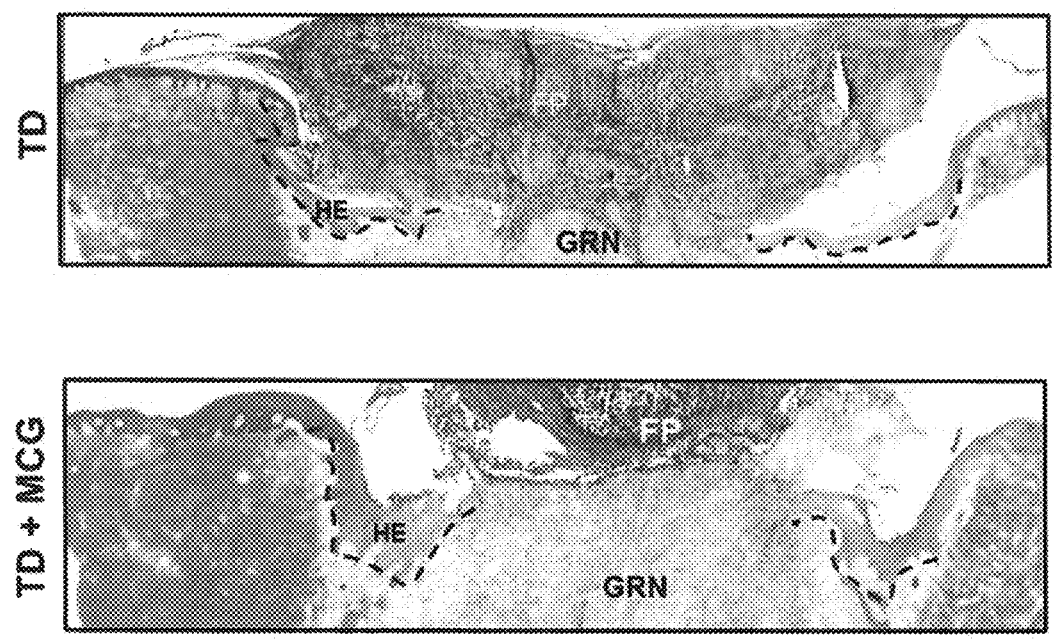
FIG. 1 shows representative histology images of the treated/untreated ischemic wounds in Example 1.

The present invention is concerned with compositions and methods for treating ischemic wounds, as well as inflammatory conditions. The compositions comprise a modified collagen gel. Exemplary modified collagen gels include Stimulen™ (Southwest Technologies, Inc., North Kansas City, Mo.). In general, the modified collagen gel comprises a dispersion of modified collagens in a glycerine or other biocompatible matrix. In one or more embodiments, the collagen gel comprises modified collagen of long and short polypeptides dispersed in an aqueous matrix comprising (consisting essentially or even consisting of) water and glycerine. The collagen gel comprises at least about 2% by weight modified collagen, preferably from about 2% to about 75% by weight modified collagen, more preferably from about 25 to about 75%, and in some cases, preferably about 52% by weight modified collagen, based upon the total weight of the composition taken as 100% by weight. The collagen gel comprises at least about 15% by weight glycerine, preferably from about 15% to about 65% by weight glycerine, more preferably from about 25% to about 65%, and in some cases, preferably about 45% by weight glycerine, based upon the total weight of the composition taken as 100% by weight. In some embodiments, the modified collagen can first be provided in a dry (powdered form), which can then be dispersed into a matrix carrier, such as glycerin and/or water before use. In one or more embodiments, the collagen is a hydrolyzed bovine collagen. In one or more embodiments, the collagens comprise primarily Type I and Type III collagens (and mainly Type I). Specific proteomic components of the preferred modified collagen gel are provided in the Table below.

TABLE 1

Proteomic Analysis of MCG Components *

| Sl. No | Description | Accession | Unigene ID | Mass (Da) | Number of significant sequences | Score |
|---|---|---|---|---|---|---|
| 1 | Hemoglobin subunit beta | HBB_BOVIN | Bt.23726 | 16001 | 7 | 685 |
| 2 | Carbonic anhydrase 2 | CAH2_BOVIN | Bt.49731 | 29096 | 10 | 650 |
| 3 | Collagen alpha- | CO1A1_BOVIN | Bt.23316 | 139880 | 3 | 321 |

TABLE 1-continued

Proteomic Analysis of MCG Components *

| Sl. No | Description | Accession | Unigene ID | Mass (Da) | Number of significant sequences | Score |
|---|---|---|---|---|---|---|
| 4 | 1 (1) chain Hemoglobin subunit alpha | HBA_BOVIN | Bt.10591 | 15175 | 5 | 319 |
| 5 | Peroxire doxin-2 | PRDX2_BOVIN | Bt.2689 | 22217 | 5 | 308 |
| 6 | Alpha-1-antiproteinase | A1AT_BOVIN | Bt.982 | 46417 | 2 | 220 |
| 7 | Serpin A3-7 | SPA37_BOVIN | Bt.55387 Bt.92049 | 47140 | 3 | 161 |
| 8 | Collagen alpha-1(III) chain | CO3A1_BOVIN | Bt.64714 | 93708 | 2 | 147 |
| 9 | Collagen alpha-2(I) chain | CO1A2_BOVIN | Bt.53485 | 129499 | 2 | 103 |
| 10 | Serpin A3-3 | SPA33_BOVIN | Bt.55387 Bt.92049 | 46411 | 2 | 85 |
| 11 | Actin, aortic smooth muscle | ACTA_BOVIN | Bt.37349 | 42381 | 2 | 79 |

Top ten most abundant proteins as detected using proteomics analysis has been presented Two unique peptides from one protein having a -b or -y ion sequence tag of five residues or better were accepted.
* From Elgharably et al., A modified collagen gel enhances healing outcome in a preclinical swine model of excisional wounds, 21 Wound Repair and Regeneration 473-481 (May-June 2013), incorporated by reference herein.

Compositions of such modified collagen gels have surprisingly been found to be useful in treating, repairing, promoting the healing of, and/or increasing the rate of healing of ischemic wounds and other inflammatory conditions (including dermal and non-dermal conditions). The term "wound" is used herein to refer to injury or disruption to living tissue caused by a lesion, cut, blow, or other impact in which the skin is cut or broken, as well as to incisions into the skin. Thus, the term encompasses incisions, cuts, lacerations, burns, avulsions, necrosis, and the like of the skin (epidermis), and can be caused accidentally or purposefully (e.g., such as through surgery). "Ischemic" wounds refer to wounds to which the flow of blood has been obstructed, restricted, or otherwise impaired, such that the wound site is deprived of oxygen, nutrients, etc. Damaged tissue deprived of adequate blood flow has a decreased ability to heal, and as such predisposes individuals to the development of chronic wounds. Unlike acute wounds, chronic ischemic conditions do not heal according to the normal wound healing process involving, inter alia, resolution of inflammation, repair of the connective tissue matrix, and angiogenesis. Accordingly, treatment protocols for acute wounds are often ineffective (and in some cases not recommended) for ischemic or other non-healing chronic wounds. It has surprisingly been found that the modified gel compositions promote wound healing even in ischemic wounds.

The compositions are useful in "treating" ischemic wound conditions and other inflammatory conditions, meaning that the composition can be applied to the site of the wound of a patient or administered (topically or injected) to a patient suffering from an inflammatory condition for the purpose of diminishing or eliminating signs, symptoms, or severity of the wound or condition.

In general, the methods comprise applying or administering a therapeutically effective amount of the composition to the site of the wound or to the patient having the inflammatory condition for a therapeutically effective period of time. In one or more embodiments, the composition is applied as a dressing to the site. The composition and/or dressing may be changed periodically, wherein a fresh amount of composition is applied to the site. Additional physiologically-acceptably non-occlusive dressings, tape, gauze, bandages, combinations thereof, and the like may be used in conjunction with the composition, according to standard wound care protocols. As used herein, the term "therapeutically effective" refers to the amount and/or time period that will elicit the biological or medical response of a tissue, system, animal or human that is being sought by a researcher or clinician, and in particular elicit some desired therapeutic effect. For example, in one or more embodiments, therapeutically effective amounts and time periods are those that reduce inflammation and initiate or promote healing of the wound site or site of dermal inflammation. One of skill in the art recognizes that an amount or time period may be considered therapeutically effective even if the wound or condition is not totally eradicated but improved partially. In one or more embodiments, a therapeutically effective amount refers to application of the modified collagen gel composition to the wound site to provide a light coating (e.g., 1/16 inch) up to about 1/8 inch of the composition or more, over the wound. The composition can be changed or re-applied daily, or multiple times per day. Likewise, the composition can be applied every other day, every three days, etc. It is noted that although conventional treatment protocols may call for packing deep wounds, it is not necessary to fill a deep wound cavity with the modified collagen gel, and the wound surfaces can simply be coated with the modified collagen gel, followed by packing the wound with a passive wound dressing to keep pressure on the wound and prevent the modified collagen gel composition from being inadvertently wiped away from the wound site. Those skilled in the art will appreciate that treatment protocols can be varied depending upon the wound, healing status, and preference of the medical practitioner.

In one or more embodiments, the methods are effective in resolving inflammation in an ischemic wound or site of dermal inflammation. The methods involve applying the composition to the wound site or site of inflammation, wherein the composition actively up-regulates macrophage function at the site to initiate the healing process (neo-vascularization), followed by timely up-regulation of anti-inflammatory factors (e.g., anti-inflammatory cytokines) to resolve inflammation and transition the in vivo healing process to angiogenesis. The methods also involve varying (e.g., increasing) the ratio of collagen type I to collagen type III at the wound site or site of dermal inflammation, comprising applying the composition to the wound site or site of inflammation. Accordingly, the methods are also effective for increasing the tensile strength of the repaired tissue site thereby reducing or minimizing the incidence of wound recurrence.

The compositions and methods are also useful for enhancing tissue perfusion at the wound site or site of inflammation by applying the composition to the wound site or site of inflammation, wherein blood flow is increased at the site.

The compositions and methods are also useful in resolving other inflammatory conditions.

Advantageously, the compositions, methods, and treatment protocols can consist of use of only the collagen gel in the treatment of the ischemic wound or inflammatory condition. In other words, no other adjunctive therapy is required to initiate or promote healing. As such, in some embodiments, the only therapeutic or "active" agent used in treating the wound or condition is preferably the modified collagen gel composition. No other antibacterial compositions, ointments, hydrogels, therapeutic dressings, and the like are needed, and can preferably be avoided under typical circumstances. Notwithstanding the foregoing, it will be understood that the methods and treatment protocols would still encompass the use of passive wound care items, such as non-occlusive bandages and gauze, etc. that can be used to cover the treated wound or inflammatory condition once the modified collagen gel has been applied or administered.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

A Modified Collagen Gel Dressing Promotes Angiogenesis in a Preclinical Swine Model of Chronic Ischemic Wounds Introduction The porcine model is widely accepted as an excellent preclinical model for human skin wounds. In this study, we utilized a well-characterized porcine model of chronic ischemic wounds. (Roy S. et al. Characterization of a preclinical model of chronic ischemic wound. Physiol Genomics 2009; 37: 211-24). Collagen is the major constituent of the dermal extracellular matrix (ECM). In addition to providing structural support, collagen dressings support granulation tissue formation by enhancing cellular chemo-attraction, differentiation, and activation. Excessive activity of proteolytic enzymes in chronic wounds threatens wound closure by degrading ECM proteins and other bioactive proteins such as growth factors. Clinical application of collagen-based products helps manage excessive proteolysis at the wound site favoring healing. The current work builds on our recent report characterizing a modified collagen gel (MCG) dressing for wound care. We have earlier reported that MCG improves wound closure in acute excisional wounds. Tissue ischemia is a critical component of chronic wound pathology. In the current report, we tested the effect MCG on wound angiogenesis using an established preclinical porcine model of experimental chronic ischemic wound.

Materials and Methods

Porcine Ischemic Flap Model

All experiments were approved by The Ohio State University's Institutional Laboratory Animal Care and Use Committee. A total of six domestic Yorkshire pigs (70-80 lbs) (Hartley Farms, Circleville, Ohio) were used in this study. Pigs (70-80 lbs) were sedated by Telazol (Zoetis, Florham Park, N.J.) and anesthetized by mask with isoflurane (3-4%). The dorsal region was shaved, and the skin was surgically prepared with alternating chlorhexidine 2% and alcohol 70% (Butler Schein, Columbus, Ohio) scrubs. Four full-thickness bipedicle skin flaps measuring 15×5 cm were created on each animal as described by Roy et al. Sterilized silicone sheets (15×5 cm) (Technical Products Inc., Decatur, Ga.) were placed underneath the flaps, and then the flap and silicone sheet edges were sutured to the adjacent skin. Laser Doppler scanning of the flaps was used to verify blood flow status and degree of ischemia.

Wounding and Treatments

A full-thickness excisional wound was created in the center of each flap using an 8-mm disposable biopsy punch. The depth of the wound was measured by the length of stainless steel section of the punch biopsy (8 mm). The wounds were created by cutting through the skin until the entire length of the stainless steel section was below the skin and the plastic shoulders (edges) of the biopsy punch were at the surface of the skin. That length was adequate to reach the subcutaneous fat in all wounds. Flap edges were sutured to adjacent skin and the underlying silicone sheet to prevent revascularization from the sides or underneath Excisional wounds on one side were treated with an MCG followed by dressing with Tegaderm™ (3M, St. Paul, Minn.). The wounds in the contralateral flaps were covered with Tegaderm™ alone as standard of dressing care (control). Treatment sides were alternated between animals to avoid any side-specific effect. All four flaps were covered with V.A.C. Drape (Owens & Minor, Mechanicsville, Va.). Dressing was changed every 5-7 days, and any accumulating wound fluid was drained as needed. On designated time points (days 7 and 21 post wounding), the entire wound tissue was harvested using a 10-mm biopsy punch, and each sample was split into three pieces for subsequent analyses: immunohistochemistry (OCT frozen) studies, RNA studies, and formalin fixed histology studies. Animals were maintained on 12-hour light-dark cycles and were euthanized after the completion of experiments.

MCG was provided as Stimulen™ gel by Southwest Technologies Inc. (North Kansas City, Mo.). According to the manufacturer, the unique formulation of the MCG represents a mixture of 52% collagen of long and short polypeptides along with glycerine, water, and fragrance. The MCG is a highly concentrated modified collagen (mainly type I) in a gel form.

Laser Doppler Scanning of Blood Flow

The MoorLDI-Mark 2 laser Doppler blood flow scanner (Moors Instruments, Axminster, United Kingdom) (resolution: 256×256 pixels in the region of interest; each pixel being an actual measurement) was used to study tissue perfusion. Laser Doppler scanning was performed after the surgical procedure and at day 21 post wounding.

Histology

Formalin-fixed paraffin-embedded or optimum cutting temperature-embedded frozen wound-edge specimens were sectioned (5 µm). The paraffin sections were deparaffinized and stained with hematoxylin & eosin (H&E) (FIG. 1), Masson's trichrome, or picrosirius red staining (PRS) using standard procedures. FIG. 1 has mosaic images showing MCG treated or TD, Tegaderm™ treated ischemic wounds on day 7 after wounding—HE: hyperproliferative epithelium; FP: fibrin plug; and GRN: granulation tissue.

Immunohistochemical staining of paraffin or frozen sections was performed using the following primary antibodies: anti-macrophage, L1 calprotectin (1:400; MAC387; Thermo Fisher Scientific Inc., Waltham, Mass.), anti-von Willebrand's factor (vWF) (Dako North America Inc., Carpinteria, Calif.), anti-Ki67 (1:400, Thermo Fisher Scientific Inc.), anti-vimentin (Sigma-Aldrich, St Louis, Mo.), and anti-CCR2 (1:250; Abcam, Cambridge, Mass.) after heat-induced epitope retrieval when necessary. Secondary antibody detection and counterstaining were performed.

Imaging

Mosaic images of whole wound sections were collected under 20× magnification guided by MosaiX software (Zeiss, Thornwood, N.Y.) and a motorized stage. Each mosaic image was generated by combining 40-50 images. Each mosaic image was generated by combining a minimum of 100 images. Between 7 and 9 high-powered representative areas from mosaic images were quantified for each data time point. Image analysis was performed by employing auto-measure software (Zeiss) for quantitation of the percentage of immuno-histochemical positive areas (expressed as % area). Confocal Scanning Laser Microscope: visualization of vascular structures within the wound tissues was achieved by using an Olympus Fluoview FV1000 spectral confocal microscope (Olympus, Pittsburgh, Pa.) under 1,000× magnification while applying an argon laser. Z-stack images were created by merging serial scans of thick tissue section (20 µm). Cell culture Human THP-1 monocytes (American Type Culture Collection, Manassas, Va.) were cultured in RPMI 1640 medium with L-glutamine supplemented with 10% FBS and 1% antibiotic antimycotic (AA) (Gibco, Auckland, New Zealand) and incubated at 37° C. in 5% $CO_2$. To differentiate THP-1 monocytes into macrophages, cells were cultured in RPMI 1640 medium with L-Glutamine supplemented with 10% heat inactivated FBS, 1% AA, and 20 ng/mL phorbol 12-myristate 13-acetate (PMA) (Sigma, St. Louis, Mo.). Supplementation THP-1 cells were incubated with or without MCG (50 mg/mL) for 24 hours. RNA was extracted from cell pellets using mirVana RNA isolation kit (Ambion, Austin, Tex.) according to the manufacturer's instructions.

RNA Isolation from Wound Tissues

Immediately after collection, wound tissue biopsies were rinsed in saline, patted dry, and snap frozen in liquid nitrogen. Grinding of the tissues was performed using a 6770 Freezer/Mill cryogenic grinder (SPEX SamplePrep, Metuchen, N.J.). Total RNA from tissue or cultured cells were extracted using mirVana RNA isolation kit. Reverse transcription and quantitative real-time polymerase chain reaction (PCR) Tissue mRNA was quantified by real-time or quantitative (Q) PCR assay using the double-stranded DNA binding dye SYBR green-I. The primer set used for the individual genes are described in Elgharably et al., Wound Rep Reg (2014) 22 720-729, incorporated by reference herein. 18s rRNA was used as a reference housekeeping gene.

Statistics

Data are reported as mean±standard error of the mean of six separate animals as indicated. As the data were not normally distributed, nonparametric statistics was used. Wilcoxon signed-rank test was used to compare control vs. MCG as the wounds were paired within the individual pigs. The significance level for this study was set at 0.05. All analyses were run using Stata 13.1 (StataCorp, College Station, Tex.).

Results

The preclinical model of chronic ischemic wounds was employed for this study. Full-thickness bipedicle flaps were surgically created on the back of pigs in such a way that interrupted blood supply from underneath and the sides of the flap. After the procedure, ischemia of flap tissue was confirmed by laser Doppler imaging of blood flow. The full-thickness excisional wounds established in the middle of the flap rested on the most poorly perfused part of the flap. By harvesting whole wound tissues at day 7 and 21 post wounding, we were able to study the effect of MCG on both early and late events of wound healing processes. Successful mounting of inflammatory response and timely resolution are necessary for proper healing of a wound. As part of investigating the inflammatory response, wound macrophages were identified in wound-edge tissue sections using an antibody against macrophage L1 protein/calprotectin (MAC387), a marker for swine tissue macrophages. Anti-MAC387 also recognizes other cells such as keratinocytes and polymorphonuclear neutrophils (PMNs). However, in this case, keratinocytes were ruled out using anti-keratin-14 (keratinocyte specific, data not shown), the cells (MAC387) did not co-localized with K14 positive cells, thus excluding keratinocytes. For PMN, the nuclear morphology is very distinct as compared with macrophages. 4',6-diamidino-2-phenylindole (DAPI; nuclear stain, blue) staining confirmed that most of the MAC387 positive cells were macrophages.

Figure 2:
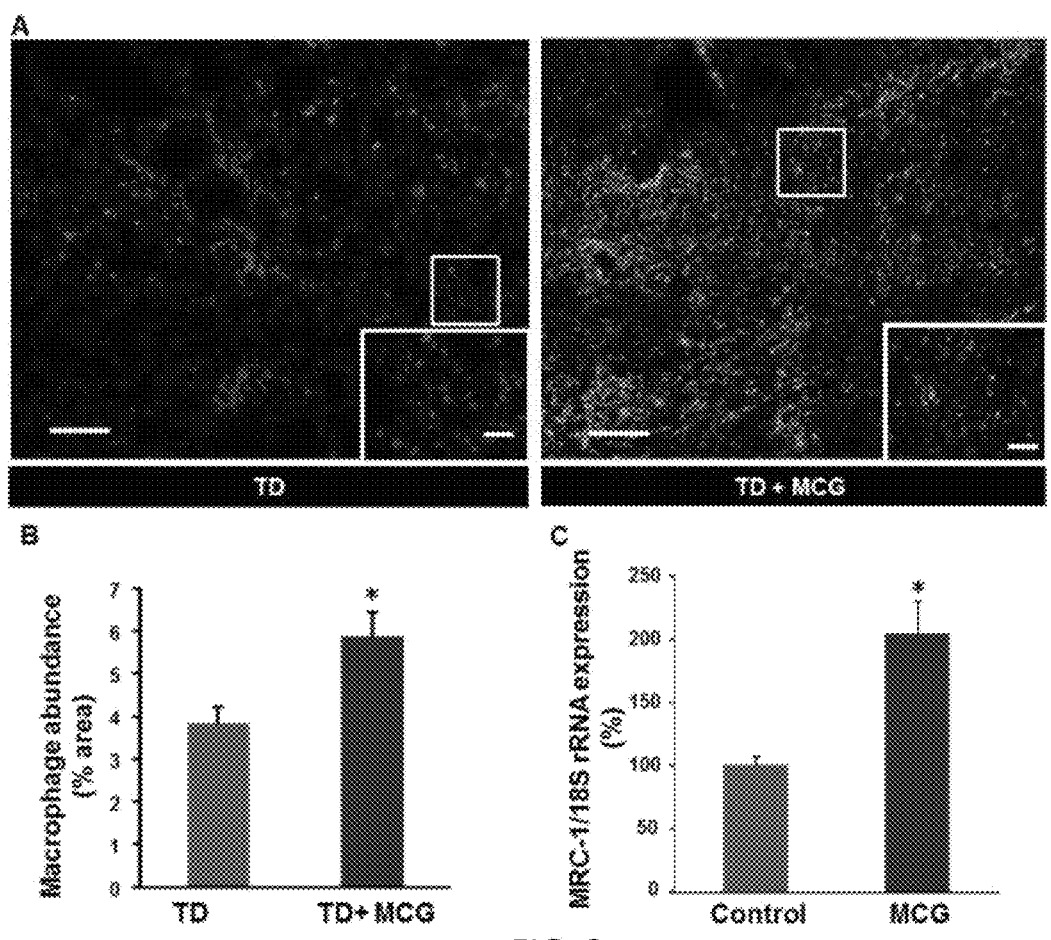
FIG. 2 shows A: representative mosaic images of wound-edge tissues that were immunostained in Example 1; B: a bar graph quantifying macrophage infiltration at day 7 post wounding in ischemic wounds treated or untreated with MCG. Data are presented as mean±SEM (n=6); *p<0.05 compared with untreated wounds; and C: up-regulation of macrophage mannose receptor 1 (MRC-1) gene expression in THP-1 differentiated human macrophages treated with MCG for 24 hour. Data are presented as % change compared with untreated cells. Data are mean±SEM (n=4); *p<0.05. TD, Tegaderm™; MCG.

Macrophage infiltration to the wound-edge tissue was significantly increased in ischemic wounds treated with MCG at day 7 post wounding compared with untreated control wounds (FIGS. 2A and B). FIG. 2A shows representative mosaic images of wound-edge tissues that were immunostained using Anti-MAC387 (macrophages, green).

The sections were counterstained with DAPI (blue). Scale bar, 200 μm. Insets are zoomed regions in the image; Scale bar, 50 μm. FIG. 2B shows a bar graph of quantitation of macrophage infiltration at day 7 post wounding in ischemic wounds treated or untreated with MCG. Data are presented as mean±SEM (n=6); *$p<0.05$ compared with untreated wounds.

This finding directed us to further investigate the effect of MCG on macrophage function in vitro. THP-1-derived macrophages treated with MCG displayed up-regulation of Mrc-1 gene expression, which is a marker for (M2) reparative macrophage subtype (FIG. 2C). The data in FIG. 2C demonstrate up-regulation of macrophage mannose receptor 1 (MRC-1) gene expression in THP-1 differentiated human macrophages treated with MCG for 24 hour. MRC-1 gene expression was measured using quantitative real-time PCR.

Figure 3:
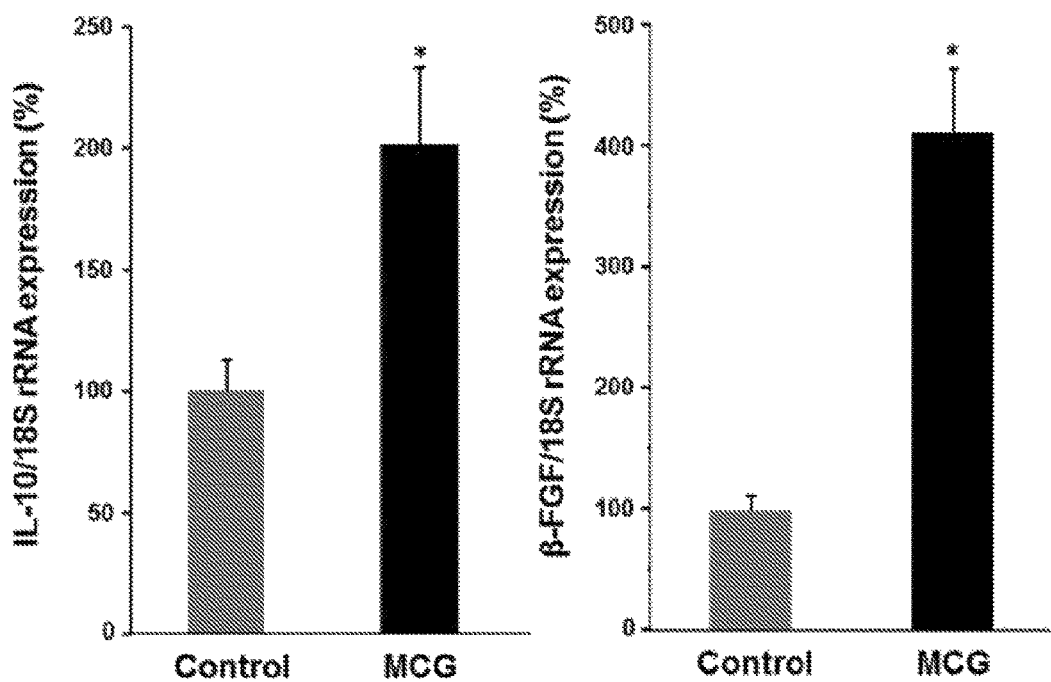
FIG. 3 graphs indicating induction of IL-10 and β-FGF genes by MCG; Up-regulation of IL-10 and β-FGF gene expression in THP-1 differentiated human macrophages treated with MCG for 24 hours. The expressions of mRNA for IL-10 and β-FGF were determined using quantitative real-time PCR. Data are presented as % change compared with untreated cells. Data are mean±SEM (n=4); *p<0.05.
Figure 4:
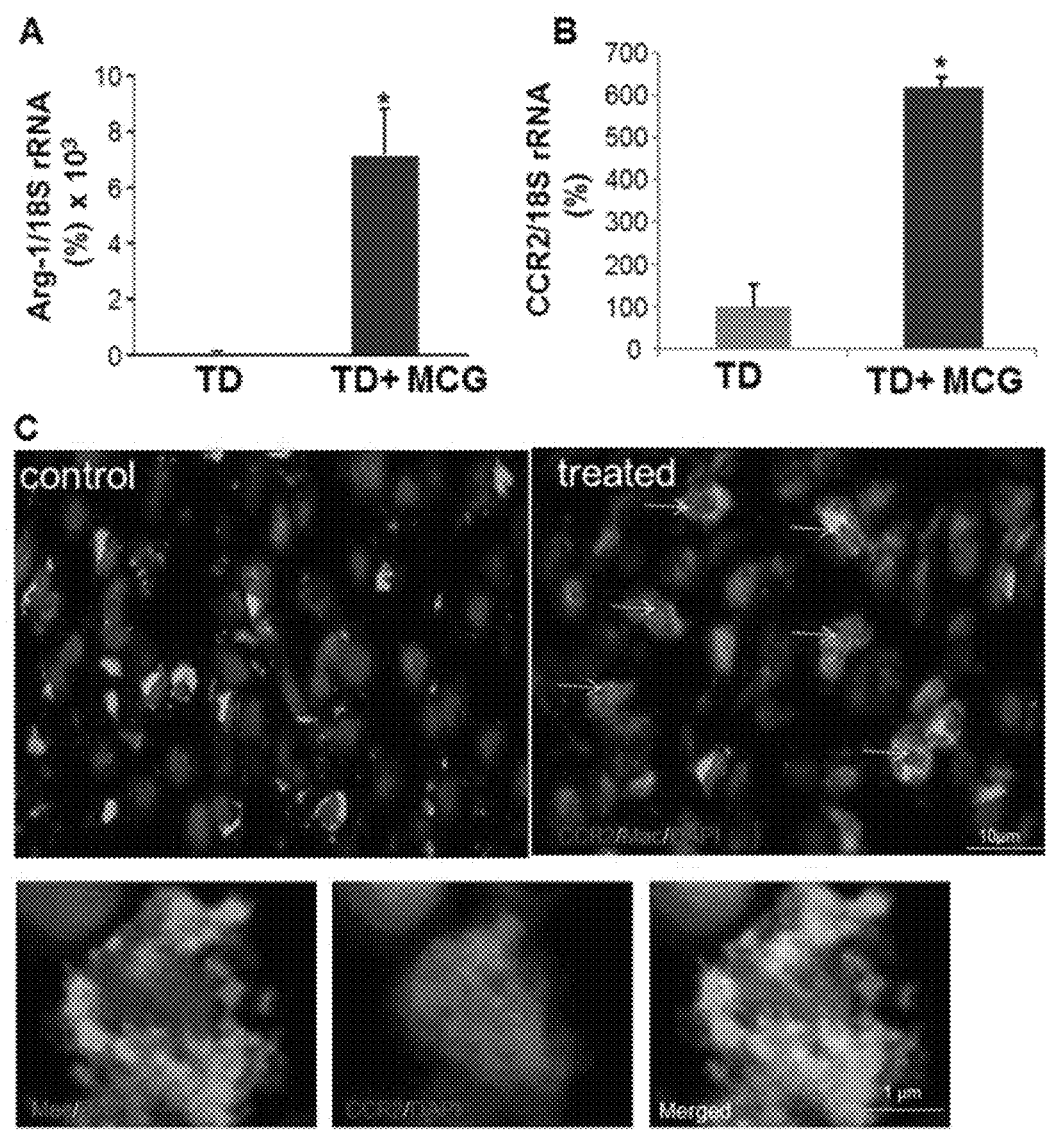
FIG. 4 shows A and B: graphs indicating increased CCR2 (M2c macrophage marker) expression in macrophages treated with MCG; and C: Representative images of control and treated wound-edge tissues immunostained using Anti-MAC387 (macrophages, green) and Anti-CCR2 E68 (M2c macrophages, red).
Figure 5:
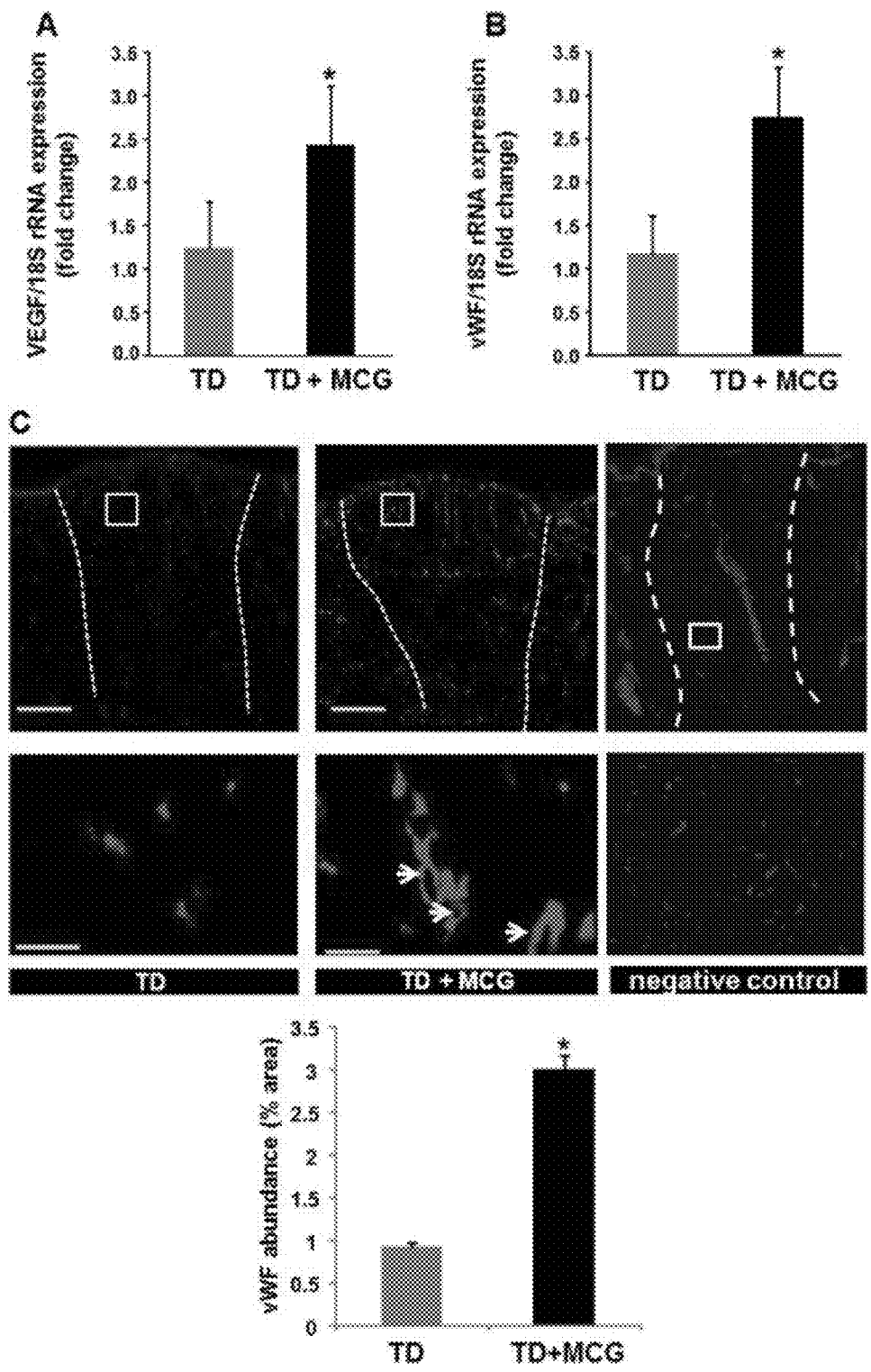
FIG. 5 shows A and B: graphs indicating that MCG promotes vascularization of ischemic wounds; and C: Representative immunofluorescence images from wound sections stained with von Willebrand factor marking vascular endothelial cells (red).

Furthermore, we observed that MCG potently induced the anti-inflammatory cytokine IL-10 and the fibroblast growth factor basic (β-FGF) gene expression (FIG. 3). To validate the in vitro finding of increased M2 macrophage marker by MCG, we studied the phenotype of wound macrophage in MCG-treated wounds. The expression of M2 macrophage markers Arg-1 and CCR2 was determined in wound tissues (FIGS. 4A and B). Real-time PCR was used to measure Arg-1 and CCR2 gene expressions in wound tissue samples at day 7 post wounding. Gene expression data are presented as % change compared with untreated wound tissues. Data are mean±SEM; *$p<0.05$. A massive induction in Arg-1 and CCR2 was noted in wound tissue following MCG treatment as compared with standard of care (TD, Tegaderm™). Recent studies indicate CCL2-CCR2 axis plays a major role in shaping macrophage polarization. In M2c macrophages, IL-10 increases expression of CCR2 and CCR5. An immunohistochemistry co-localization study was performed with anti-L1 (Macrophage, green) and anti-CCR2 (M2c macrophage, red) (FIG. 4C). The sections were counterstained with DAPI (blue). Scale bar, 10 μm. Insets are zoomed regions in the image, Scale bar, 1 μm. Increased CCR2 positive macrophages in wound tissue 7 days post wounding was observed suggesting that either promotion of M2 macrophages recruitment or increased conversion of wound site macrophages to M2 phenotype. In vitro data showing a direct effect of MCG on macrophages by increasing expression of M2 marker supports the latter proposition, i.e., increased conversion to M2 phenotype by MCG. One of the potent angiogenic factors that promote wound revascularization is vascular endothelial growth factor (VEGF). We observed significant increase of VEGF gene expression at day 7 post wounding in wound-edge tissue treated with MCG compared with corresponding control (FIG. 5A). In concordance with that observation, higher abundance of endothelial cell marker vWF was detected in wound-edge tissues of MCG-treated wounds (FIG. 5B). Total RNA was isolated from wound-edge tissue material stored in liquid nitrogen. Real-time PCR was used to measure VEGF and vWF gene expressions in samples at day 7 post wounding. Gene expression data are presented as % change compared with untreated wound tissues. Data are mean±SEM (n=6); *$p<0.05$. Histological quantitation of endothelial cells abundance in wound-edge tissues showed a markedly elevated count in wounds treated with MCG reflecting increased endothelial cell proliferation (FIG. 5C). Scale bar, 500 μm. Lower panel are zoomed regions in the images on top; Scale bar, 50 μm. Negative control image shows specificity of the anti-vWF staining. The section was counterstained with DAPI (blue, nuclear) to show the cells present in the section. Bar graph shows quantitation of the endothelial cells in MCG-treated or untreated ischemic wounds at day 21 post wounding. Data are presented as mean±SEM (n=6); *$p<0.05$ compared with untreated wounds. White dashed lines indicate the edges of the wound. TD, Tegaderm™; MCG.

Figure 6:
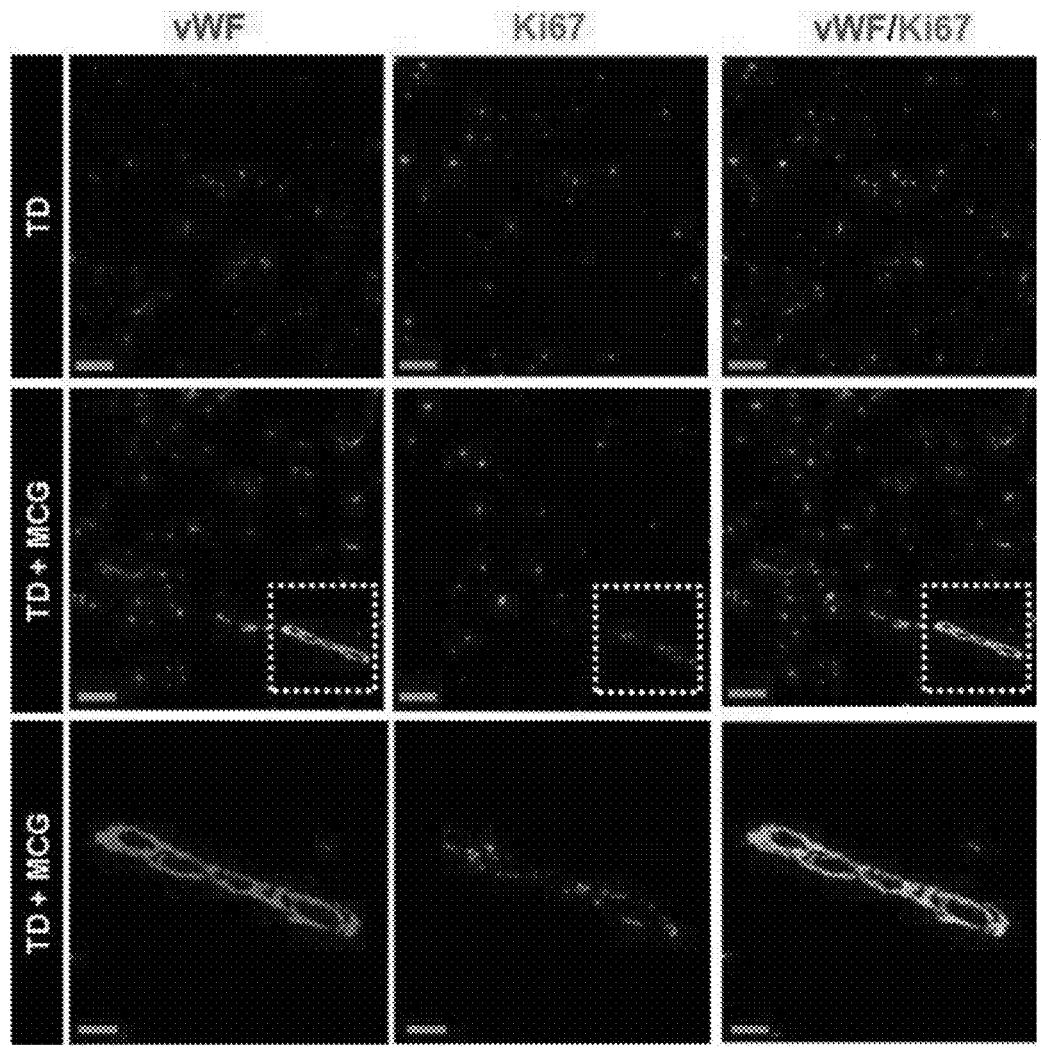
FIG. 6 shows images demonstrating vascularization of MCG-treated ischemic wounds was enhanced by endothelial cell proliferation based upon representative immunofluorescence images of wound sections (8 µm) at day 21 post wounding stained using Ki67 (marker of proliferating cells, green) and von Willebrand factor (endothelial cells, red) antibodies.

MCG-treated ischemic wounds also had markedly higher abundance of endothelial cells 21 days post wounding indicating that the favorable effect of MCG on endothelial cell proliferation was persistent. Dual immunofluorescence staining technique was employed to co-localize cell-proliferation marker Ki67 within endothelial cells. Ki67 is a nuclear protein that is associated with cellular proliferation. Quantitative analysis of Ki67 in vWF+ endothelial cells using an automated software-based methodology revealed that MCG treatment markedly enhanced endothelial cell proliferation at the ischemic wound-edge tissue (FIG. 6). A marked increase of proliferating endothelial cells in MCG-treated ischemic wounds compared with control wounds as evident by co-localization of Ki67 within vascular structures (yellow areas in merged images) was noticed. The bottom panels are zoomed regions within the dashed white boxes in the corresponding middle panels. Top and middle panels scale bars, 50 μm. Bottom panel scale bar, 20 μm.

Figure 7:
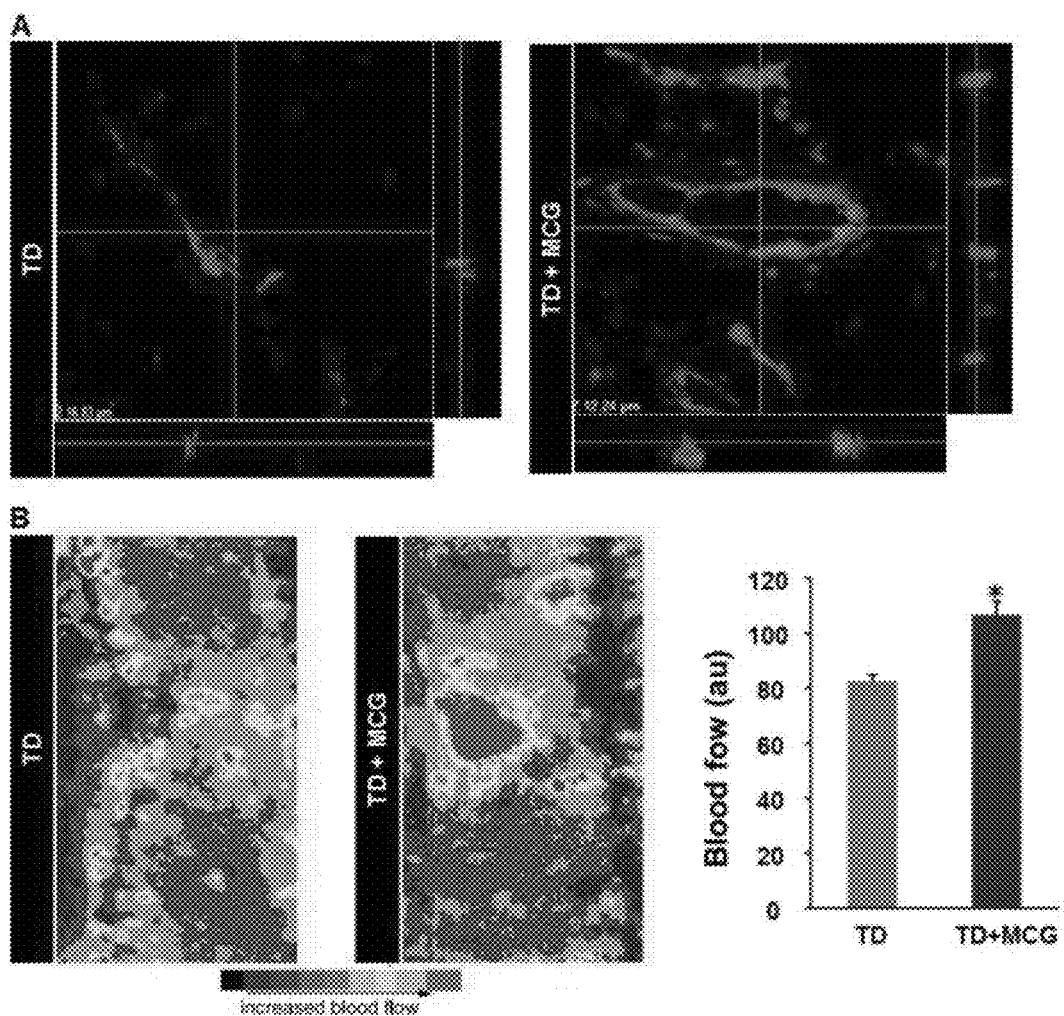
FIG. 7 shows data demonstrating vascularization of MCG-treated ischemic wounds displayed improved maturity and functionality. A: Wound tissue sections immunostained with an antibody against von Willebrand factor (red) followed by counterstaining with DAPI (blue), viewed with a confocal laser scanning microscopy at a 1,000× magnification. Z-stack images were created by merging serial scans of thick tissue section (20 µm); and B: Laser Doppler images of ischemic flaps on the back of the pig at day 21 post wounding.

Next, we sought to address the quality and functionality of vascular structures at the wound edge. Thick wound-edge tissue sections (20 μm) were immuno-stained for vWF and examined using confocal laser scanning microscope (CLSM). Qualitative analyses of wound-edge vascular structures were performed using CLSM by creating Z-stack merged images. Interestingly, on day 21 post wounding, MCG-treated ischemic wounds displayed more mature and thick vascular formations, whereas control wound-edge tissue featured a scanty distribution of thin vascular structures (FIG. 7A). Note increased mature vascular structures in MCG-treated ischemic wounds compared with untreated wounds in the x/y plane, whereas the x/z and y/z planes display the thickness of the vascular structures in the tissue section.

To determine blood flow, we applied laser Doppler imaging technology. Laser Doppler scanning is a reliable and applicable method that provides information about tissues' perfusion without physical contact. At day 21 post wounding, scanning of flap tissues by laser Doppler showed significant increase of blood flow to wound tissue treated with MCG compared with corresponding control wounds (FIG. 7B). Marked increase in blood flow (red) was noted in ischemic wounds treated with MCG. Bar graph represents the quantitative data from laser Doppler analysis. Data presented as mean±SEM (n=6); *$p<0.05$ compared with untreated wounds.

Figure 8:
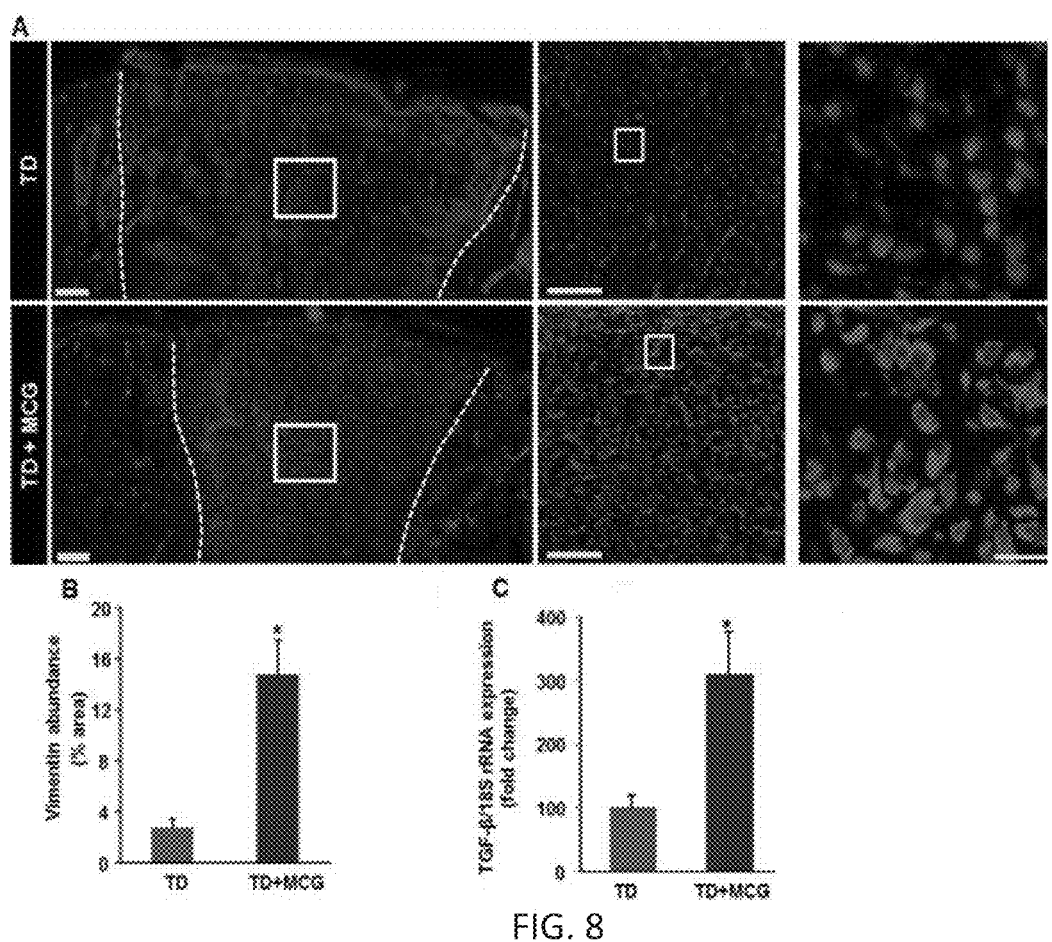
FIG. 8 shows data demonstrating increased vimentin expression in ischemic wounds treated with MCG. A: Mosaic images of wound tissue sections that were immune-stained with antivimentin (red) and DAPI (blue). (B) Bar graph shows quantitation of vimentin expression at day 21 post wounding in MCG-treated or -untreated ischemic wounds. (C) Real-time PCR was used to measure TGF-β gene expression in wound tissue samples of day 7 post wounding.

Collectively, MCG-treated ischemic wounds had higher abundance of proliferating endothelial cells that formed mature and functional vascular structures with an increase of blood flow to the wound site. Fibroblast proliferation is a key driver of the proliferative phase of wound healing. Fibroblasts synthesize collagen and other ECM components that form the scaffold necessary for the migration and proliferation of other cell types involved in wound repair. Vimentin has been used routinely as a marker for dermal fibroblasts. Vimentin is one of the intermediate filaments expressed in cells of mesenchymal origin. Other cells of mesenchymal origin such as pericytes may express vimentin. Immunofluorescence staining data revealed that vimentin expression in MCG-treated ischemic wounds was significantly higher on day 21 post wounding compared with untreated wounds (FIGS. 8A and B). White dashed lines indicate the edges of the wound. Middle and right panels are zooms of the boxed areas within the images in the left panels. Scale bar, 100 µm (middle); Scale bar, 10 µm. Data are presented as mean±SEM (n=6); *p<0.05 compared with untreated wounds. Furthermore, on day 7 post wounding, wound-edge tissue samples from MCG-treated group showed up-regulation of TGF-β gene expression compared with corresponding control wounds (FIG. 8C). Gene expression data are presented as % change compared with untreated control wound tissues. Data are mean±SEM (n=4); *p<0.05. TD, Tegaderm™; MCG.

Figure 9:
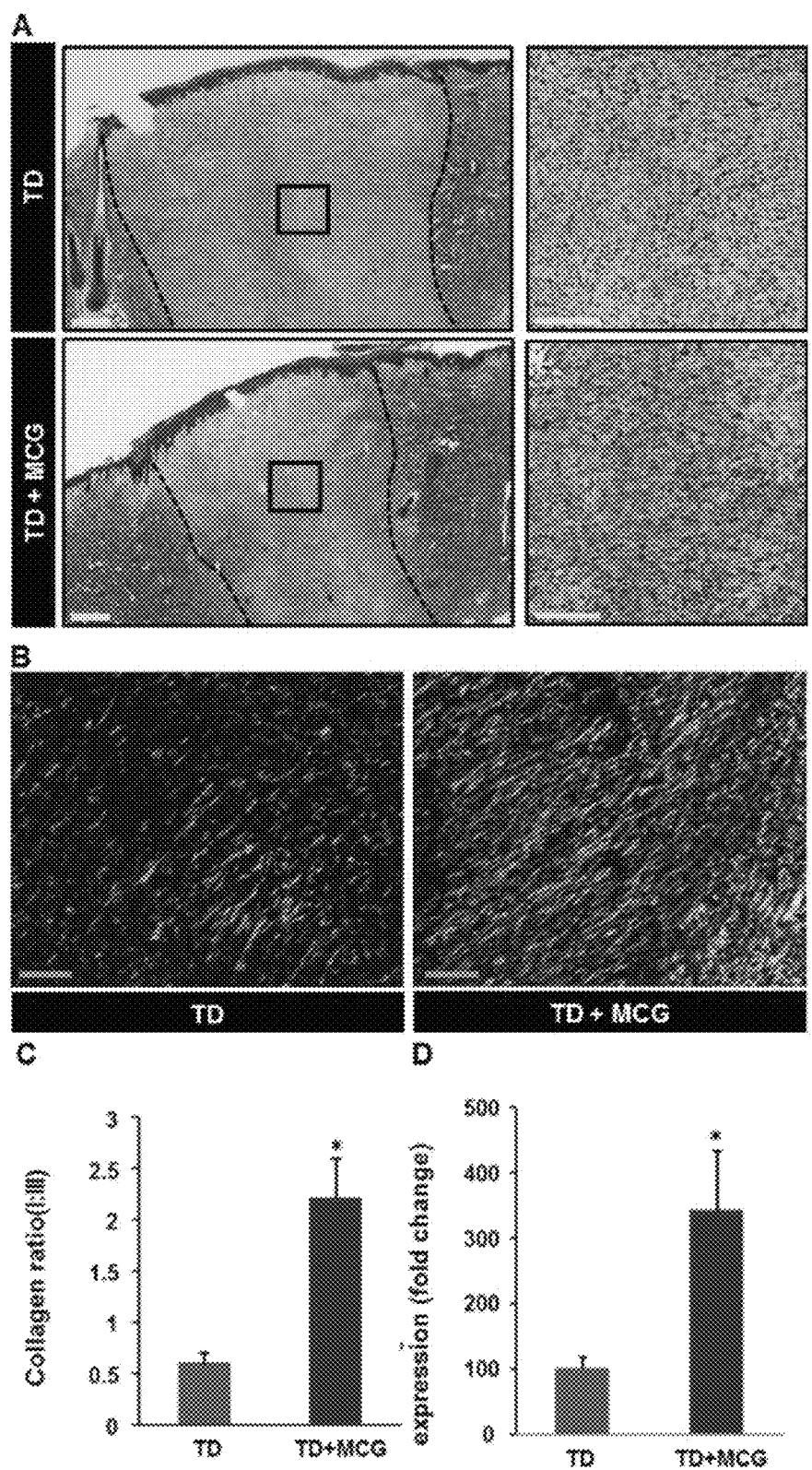
FIG. 9 show data demonstrating mature collagen deposition in ischemic wounds treated with MCG. A: Representative images of formalin-fixed paraffin-embedded (FFPE) wound biopsy sections (5 µm) stained using Masson's trichrome; B: Representative images from FFPE wound tissue biopsy sections stained using picrosirius red staining (PRS); and C: Collagen type I gene expression in day 7 ischemic wound tissues was quantified using real-time PCR.

TGF-β is one of the regulatory growth factors that contribute to fibroblasts' recruitment and stimulation of collagen expression in healing wounds. These two findings, along with cyto-morphological properties of vimentin positive structures, point to the conclusion that MCG-treated ischemic wounds were heavily populated by fibroblasts on day 21 post wounding. Appropriate collagen deposition helps build tensile strength of the nascent tissue. Histological characterization of collagen in pair-matched wounds was performed through Masson's trichrome and PRS. Masson's trichrome staining of wound-edge tissues showed higher deposition of mature collagen fibers in MCG-treated ischemic wounds (FIG. 9A). This staining results in blue-black nuclei, blue collagen, and light red or pink cytoplasm. Epidermal cells appear reddish. Scale bar, 200 µm. Black dashed lines indicate the edges of the wound. Right panels are the zooms of the boxed areas within the images in the left panels. Scale bar, 100 µm. Bar graph shows quantitation of collagen abundance in MCG treated or -untreated ischemic wounds on day 21 post wounding. Data are presented as mean±SEM (n=6); *p<0.05 compared with untreated wounds. PRS was used to identify both types I and III collagen fibers at the wound site. In tissues stained with PRS, type I collagen (thick fibers) is viewed as yellow orange birefringence, whereas type III (thin fibers) is viewed as green birefringence under polarized light microscope. Significant increase of collagen type I:III deposition was noted in MCG-treated wounds (FIG. 9B). This stain can be used to distinguish between type I and type III collagen in wound tissues; type I (thick fibers) appears yellow-orange birefringence, whereas type III (thin fibers) appears green birefringence when viewed under polarized light microscope. Showing is a marked increase of collagen I:III ratio (yellow-orange fibers to green fibers) in MCG-treated ischemic wounds compared with untreated control wounds. Scale bar, 100 µm. This histological phenotypic change was supported by up-regulation of collagen type I gene expression in MCG-treated ischemic wounds in day 7 wound tissue samples (FIG. 9C). Gene expression data are presented as % change compared with MCG-untreated control wound tissues. Data are mean±SEM (n=6); *p<0.05.

Discussion

Management of ischemic tissue ulceration represents a substantial clinical challenge. Excessive proteolysis at the wound site results in uncontrolled degradation of the ECM and growth factors that are essential for normal tissue repair. From a clinical point of view, collagen-based products are safe and easily applicable wound dressings that can be combined with other modalities. The mechanism of action of collagen-based products is poorly understood. Exogenous collagen to wounds has been shown to promote hemostasis and chemotaxis. In addition, collagen dressings act as matrices for new cell ingrowth. The current report for the first time shows efficacy of MCG, a collagen-based dressing, in the harsh environment of ischemic wounds by resolving inflammation and promoting wound angiogenesis. Failure to resolve inflammatory state in a timely manner eventually leads to tissue necrosis with increased risk of serious complications such as secondary infection and amputation. A unique feature of collagen-based products is that they are effective in managing excessive proteolytic enzyme activity. Furthermore, exogenously added collagen is claimed to replenish the wound site ECM, thereby providing a scaffold for cell recruitment and migration. Interactions between the ECM molecules and cell surface receptors regulate cellular and molecular events of the proliferative phase including epithelialization, angiogenesis, and fibroplasia.

Wound site macrophages represent key drivers of wound repair in the inflammatory phase. Monocytes recruited to injury site differentiate to pro-inflammatory macrophages (M1) or anti-inflammatory/pro-angiogenic macrophages (M2). The M1 macrophages are responsible for clearing of infectious agents through secretion of pro-inflammatory cytokines and chemokines that stimulate the immune response. A switch from pro-inflammatory to anti-inflammatory macrophage phenotypes occurs following engulfment of apoptotic inflammatory cells also known as efferocytosis. M2 macrophages help resolve inflammation in a timely manner and induce granulation tissue formation through enhancing ECM synthesis, angiogenesis, fibroblast proliferation, and epithelialization. Imbalance between pro- and anti-inflammatory signals in the direction of the former results in persistent wound inflammation and failure to enter the reparative phase of healing. Higher M1:M2 macrophage ratio results in wound chronicity. Our recent work shows that macrophage dysfunction with persistent pro-inflammatory signaling is responsible for chronicity of diabetic wounds. MCG enhanced macrophage recruitment to the ischemic wound site in the early phase is indicative of a strong inflammatory response. Mrc-1 (mannose receptor c) expression is recognized as a marker for the M2 macrophage phenotype. Increased CCR2 is a marker for IL-10-induced M2c macrophages.

We recognize that increased expression of only one M2c macrophage (CCR2) in MCG-treated wounds does not conclusively show that MCG promotes M2 macrophage switching. However, this evidence along with in vitro finding on isolated macrophage (Mrc-1) and increased expression of M2 macrophage markers (Arg-1 and CCR2) strongly suggests a potential role of MCG in macrophage polarization in wounds. IL-10 is a major anti-inflammatory agent that helps execute scar-minimized regenerative healing of fetal wounds. β-FGF is a key growth factor that promotes granulation tissue formation and wound closure through stimulation of wound angiogenesis, fibroblasts proliferation, and migration. Ischemic wounds show delayed macrophage recruitment to the wound site. Taken together, the current study shows that even under conditions of ischemia, MCG promoted macrophage recruitment to wounds. Furthermore, presence of MCG helped switching of M1 macrophages to M2 phenotype suggesting MCG not only increases macrophage recruitment but also helps in resolution of prolonged inflammation, a characteristics of ischemic wounds.

Ischemic wounds lack blood-borne products such as oxygen, nutrients, and circulating cells that are necessary for the tissue repair process. Enhancing tissue perfusion therefore represents a useful strategy to rescue ischemic wounds. A robust inflammatory response is known to drive wound neovascularization. In this context, wound site macrophages play a major role. Macrophages secrete pro-angiogenic factors such as VEGF. Signaling between endothelial cell surface receptors and ECM molecules, such as collagen, stimulates migration and proliferation of endothelial cells. Also, it has been shown that the three-dimensional structure of the collagen matrix helps endothelial cells to organize into mature vascular structures. An abundance of proliferating endothelial cells associated with mature capillary-like structures in MCG-treated wound-edge tissue is indicative of a potent effect of the dressing on wound vascularization. This contention is supported by improved wound site blood flow data. Collagen deposition at the site of healing empowers the nascent tissue with tensile strength that helps prevent wound reopening. Collagen deposition is known to be inadequate in ischemic wounds that accounts for wound dehiscence and failure to close. At the wound site, collagen synthesis is primarily contributed by fibroblasts. Of the several factors that determine the recruitment and proliferation of fibroblasts to the wound site, ECM and growth factors represent major components. Transforming growth factor-β (TGF-β) promotes fibroblast migration, proliferation, and collagen production. Increased expression of TGF-β together with increased fibroblast abundance in MCG-treated ischemic wounds suggested increased collagen synthesis in these wounds. Indeed, abundant mature collagen fibers were identified in MCG treated. Importantly, collagen type I dominated over collagen type III. Such increased collagen type I:III ratio is crucial for appropriate wound tensile strength to support the growth of vascularized granulation tissue and to prevent dehiscence. In summary, this study provides novel insight into the mechanism of action of a collagen-based dressing as it relates to outcomes of experimental ischemic wounds. Earlier we showed efficacy of collagen-based MCG dressing improved inflammatory cell infiltration and angiogenesis in acute excisional wound. Using a porcine ischemic wound model, we have reported that such wounds exhibit prolonged inflammatory phase and poor angiogenesis. The current study shows that even under conditions of ischemia, i.e., oxygen and nutrient deprivation, MCG is effective in bolstering a reparative inflammatory response followed by improved wound vascularization and favorable organization of the ECM. Taken together, the observations of the current study warrant testing the efficacy of MCG in a clinical setting.

Example 2

A Collagen Gel Based Wound Dressing Resolves Inflammation Through a miR-21 Dependent M2 Macrophage Polarization Reference is made to FIGS. 10-17. The data indicates that MCG recruits higher levels of initial macrophage response to the site of inflammation. MCG also facilitates resolution of inflammation sooner in the healing process by signaling the switch of pro-inflammatory macrophages to reparative macrophages faster than untreated sites. The data supports potential use of MCG in a wide variety of inflammatory conditions, and that it may have beneficial impact on a wide variety of pathways for inflammatory disorders.

Figure 10:
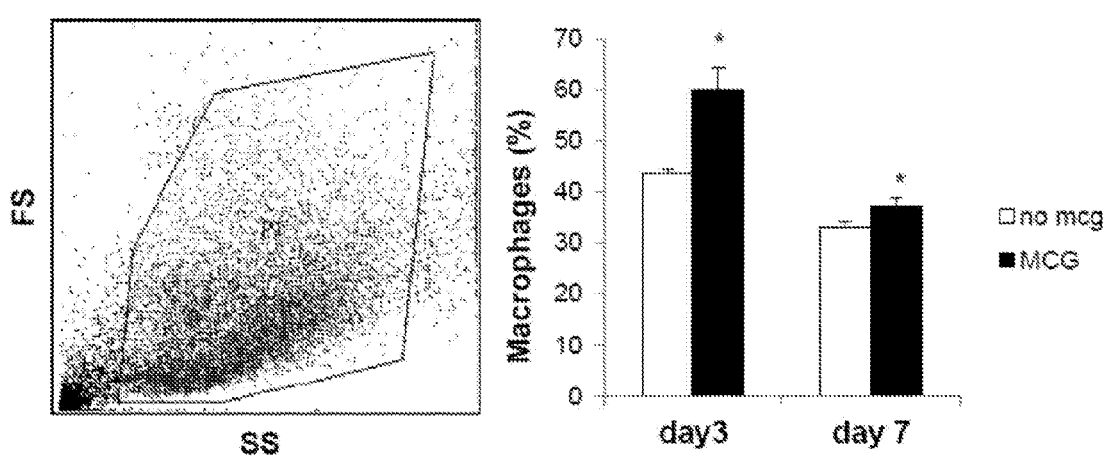
FIG. 10 shows data from Example 2 including A: a representative scatter plot of cells harvested from sponges at day-3 post implantation subjected to flow cytometry analysis and gated for quantification; and B: a graph of FITC-conjugated F4/80 positive cells quantified from the gated cell populations. Data are mean±SD (n=6); *$p<0.05$ compared to untreated cells.

In FIG. 10, cells were harvested from sponges pre-treated with MCG on Day 3 post implantation subjected to flow cytometry analysis and gated for quantification. The FITC-conjugated F4/80 positive cells were quantified from the gated cell populations. Data are mean±SD (n=6); *p<0.05 compared to untreated cells. As shown in FIG. 10, based upon flow cytometry analysis, the data indicates that MCG recruits higher levels of macrophages to the wound (initial and pro-inflammatory M1 macrophage stages) earlier in the inflammatory process.

Figure 11:
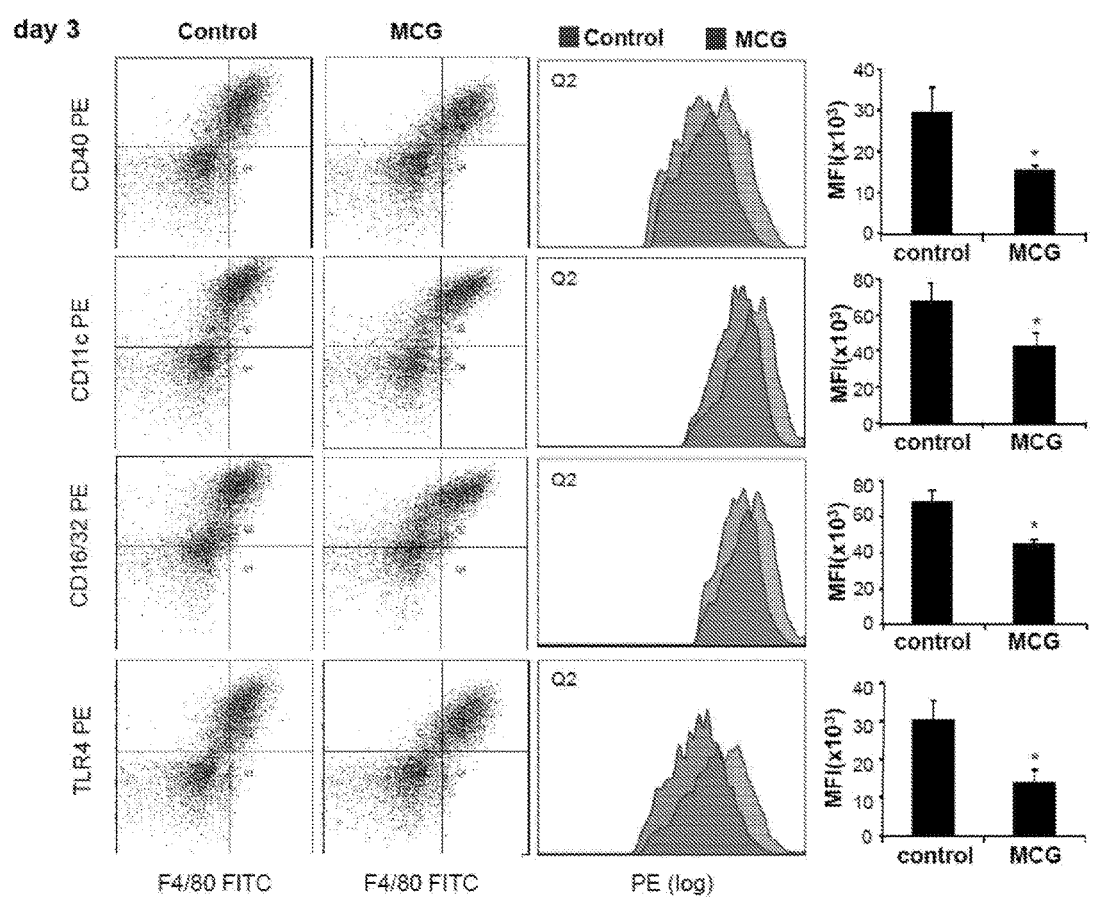
FIG. 11 shows representative four-quadrant dot plots (column 1 & 2), histograms of FITC+ and PE+ cells (column 3), and quantitative results expressed as MFI of double positive cells (column 4) in the early inflammatory phase of wound healing from Example 2. Data are mean±SD (n=6); *$p<0.05$.

In FIG. 11, cells were harvested from sponges pre-treated with MCG on Day 3 and subjected to flow cytometry analysis and gated for quantification. Data are mean±SD (n=6); *p<0.05 compared to untreated cells. The data indicates that although MCG recruits higher levels of wound macrophages to the wound (initial and pro-inflammatory M1 macrophage stages) early in the inflammatory process, as shown in FIG. 10, the level of pro-inflammatory macrophages subsides quicker than the untreated control, indicative of inflammation levels resolving earlier in the process. As such, there is a lower abundance of Wound Macrophage M1 Phenotype in response to MCG in the Early Inflammatory Phase.

Figure 12:
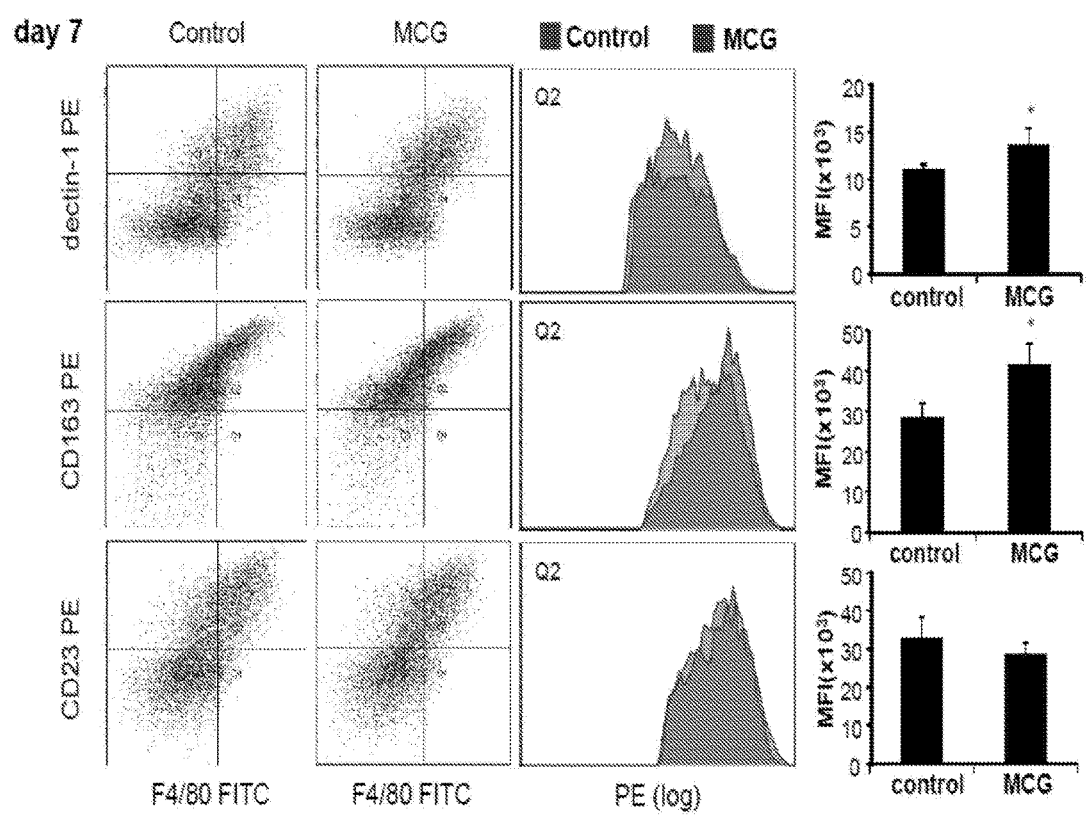
FIG. 12 shows representative four-quadrant dot plots (column 1 & 2), histograms of FITC+ and PE+ cells (column 3), and quantitative results expressed as MFI of double positive cells (column 4) in the late inflammatory phase of wound healing from Example 2. Data are mean±SD (n=6); *$p<0.05$.

In FIG. 12, cells harvested from pretreated sponges 7 days post implantation and stained with fluorescent-tagged FITC anti-F4/80 and PE M2 markers, then subjected to flow cytometry analysis. Data are mean±SD (n=6); *p<0.05. The data indicates that during the later stages of the inflammatory process, MCG facilitates a quicker switch from the pro-inflammatory M1 macrophage phenotype to the reparative M2 macrophage phenotype. Higher levels of reparative macrophages are seen in the presence of MCG, as compared to the controls, in the late inflammatory phase. Thus, not only does MCG initially recruit a higher macrophage response to the inflammatory process, but facilitates and earlier switch to the reparative phenotype, resulting in an earlier start to the resolution of the inflammatory response.

Figure 13:
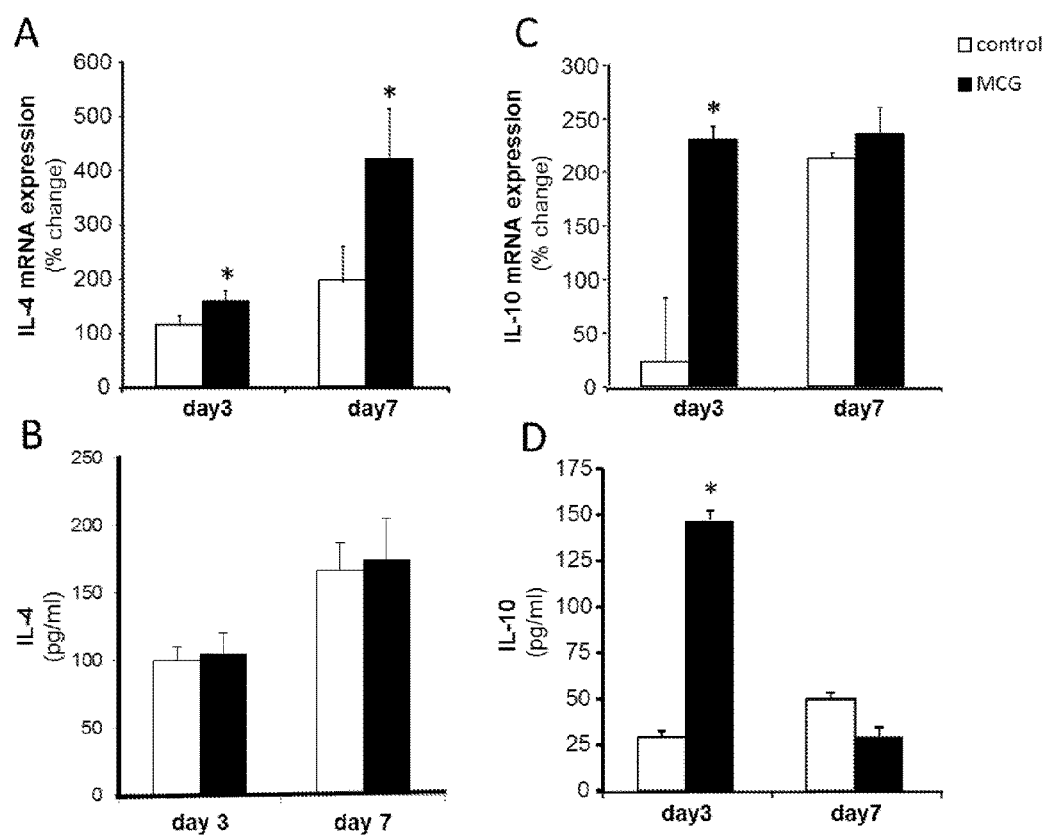
FIG. 13 shows graphs indicating up-regulation of IL-4 (A&B) and IL-10(C&D) gene expression & protein production in mouse inflammatory cells collected from MCG-treated sponges at different time points.

In FIG. 13, the data relates to measurement of anti-inflammatory cytokines (expression and protein levels) in the presence and absence of MCG. The data shows upregulation of IL-4 and IL-10 gene expression & protein production in mouse inflammatory cells collected from MCG-treated sponges at different time points. Both genes expression were measured using quantitative real-time PCR. Protein production was measured by ELISA. Data are presented as % change compared to untreated cells. Data are mean±SD (n=6); *p<0.05. The data indicates that the level of anti-inflammatory cytokines IL-4 and IL-10 are higher in the presence of MCG as compared to the controls. In particular, the level of IL-10 expression is ten times higher than the controls at day 3 (early in the inflammatory process), while the level of IL-10 protein is about six times higher at day 3.

Figure 14:
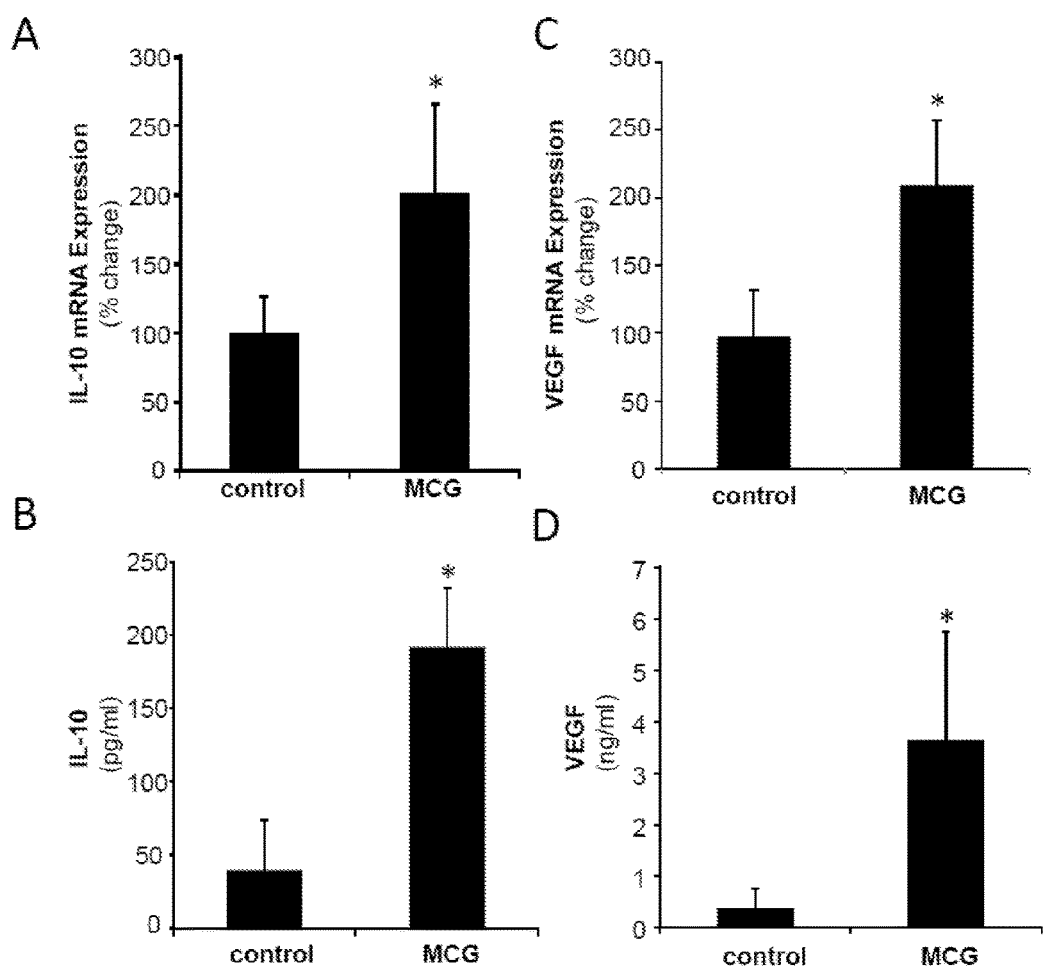
FIG. 14 shows graphs indicating up-regulation of IL-10 (A&B) and VEGF(C&D) gene expression and protein production in THP-1 differentiated human macrophages treated with MCG for 72 h.

FIG. 14 shows graphs demonstrating increased IL-10 & VEGF production by THP-1 derived macrophages after treatment with MCG in vitro, based upon increases in gene expression and protein production in THP-1 differentiated human macrophages treated with MCG for 72 h. Both genes expression were measured using quantitative real-time PCR. Protein production was measured by ELISA. Data are presented as % change compared to untreated cells. Data are mean±SD (n=4); *p<0.05.

Figure 15:
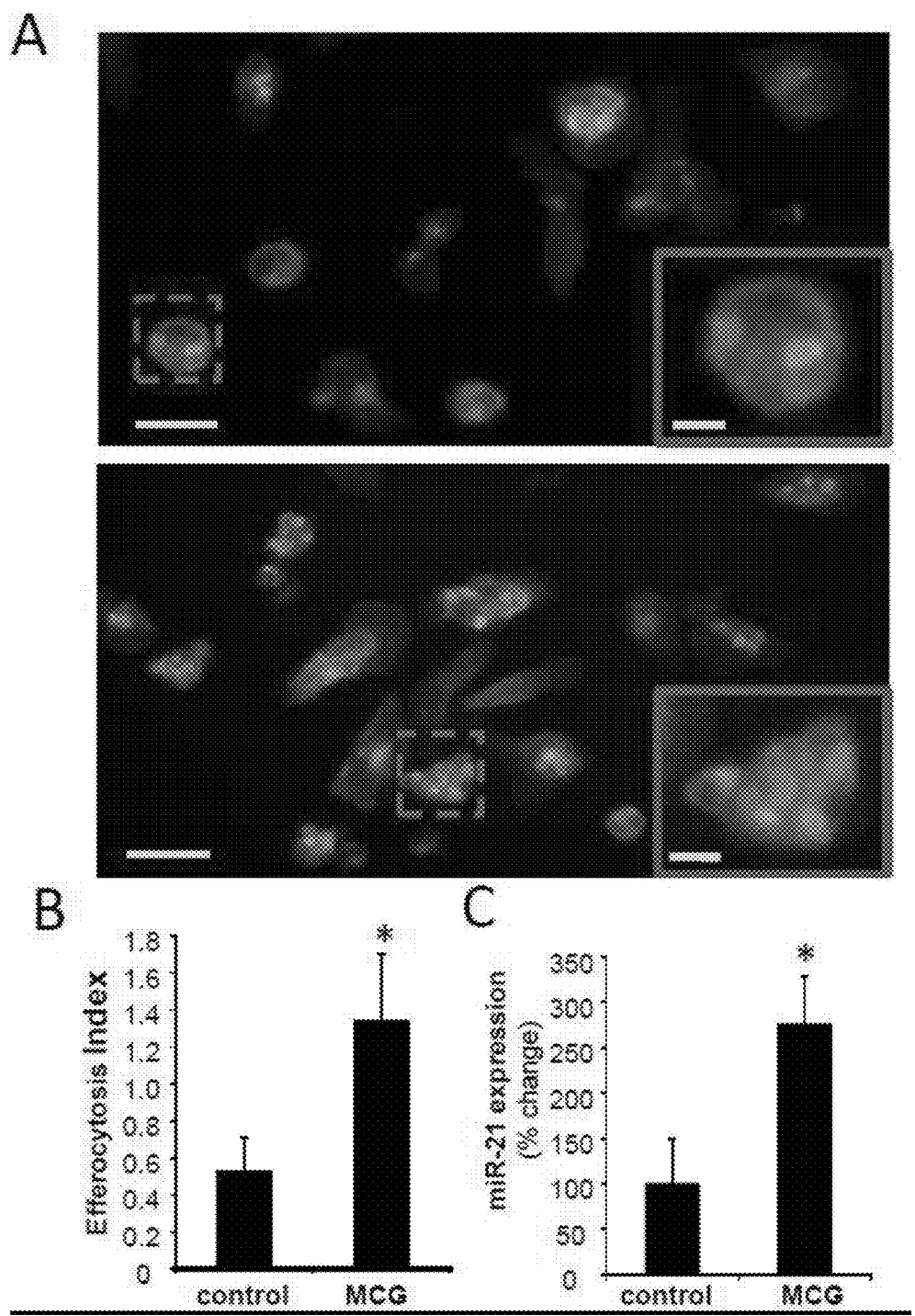
FIG. 15 shows A: Representative images showing harvested MCG-treated macrophages (green, CD68) cultured with apoptotic thymocytes (red, CMTMR cell tracker); B: efferocytosis scoring of thymocytes engulfed by macrophages, calculated as total number of apoptotic cells engulfed by macrophages in a field of view divided by total number of macrophage presented in the view; and C: Mir-21 expression in mouse inflammatory cells collected from MCG-treated sponges at day 3 post implantation, presented as % change compared to untreated cells.

In vitro work carried out using human THP-1 derived macrophages is illustrated in FIG. 15. The macrophages were incubated with MCG alone. The data demonstrates that MCG bolsters phagocytosis and induces mir-21 expression in mouse macrophages. The MCG-treated macrophages (green, CD68) were cultured with apoptotic thymocytes (red, CMTMR cell tracker). Cells were counterstained with DAPI (nuclear, blue). Efferocytosis scoring of thymocytes engulfed by macrophages was carried out and calculated as total number of apoptotic cells engulfed by macrophages in a field of view divided by total number of macrophage presented in the view. The Mir-21 expression in mouse inflammatory cells collected from MCG-treated sponges at day 3 post implantation was determined, presented as % change compared to untreated cells. Data are mean±SD (n=4); *p<0.05. The data indicates that MCG is directly responsible for signaling the macrophage activity and increasing IL-10 expression and protein levels. MCG is also responsible for inducing VEGF expression and increased protein levels as compared to the controls.

Figure 16:
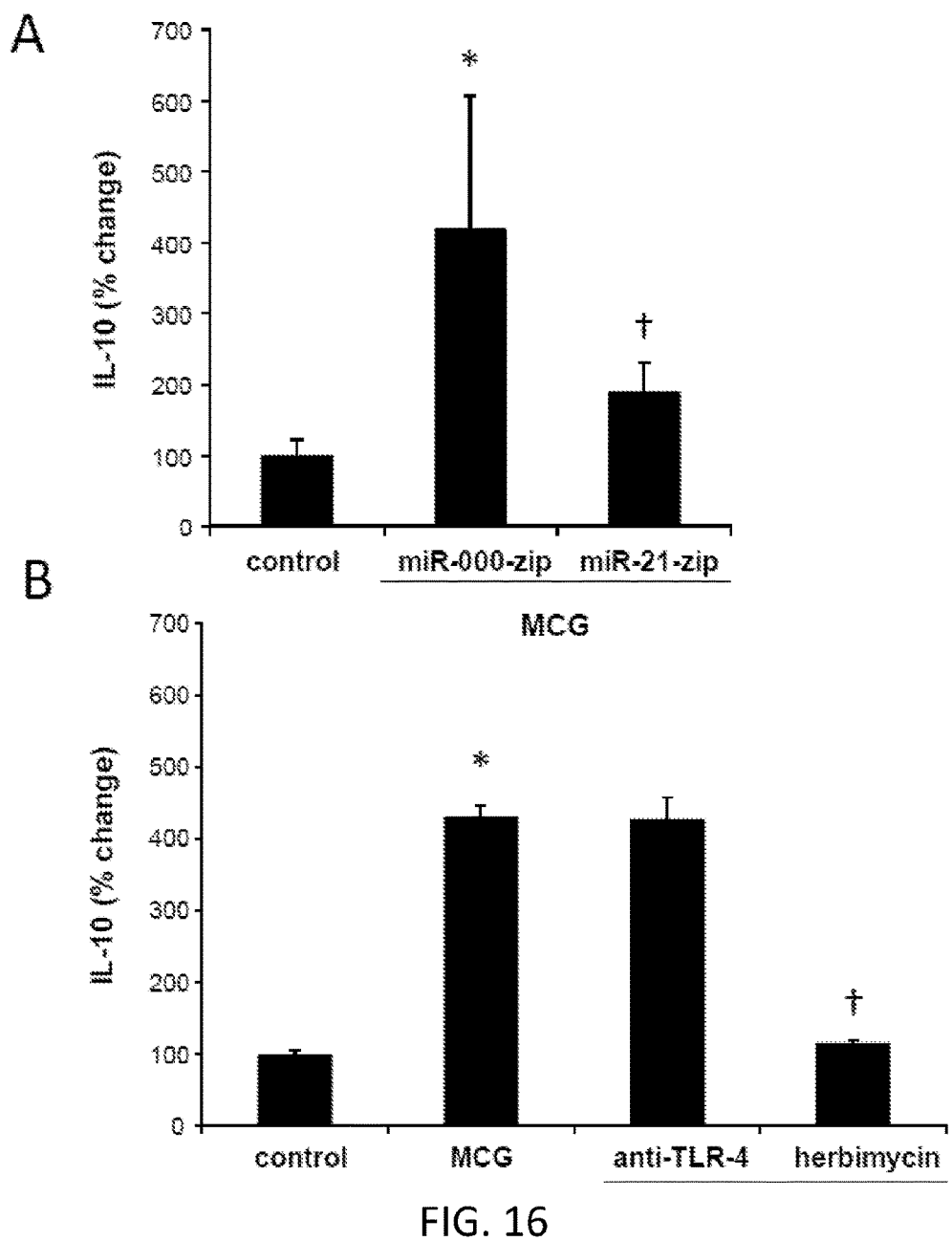
FIG. 16 shows graphs of A: IL-10 production in miR-000-zip or miR-21-zip cells after treatment with MCG; and B: IL-10 production by MCG in differentiated THP-1 cells pre-treated with anti-TLR-4 antibody, Herbimycin, or vehicle.

In FIG. 16, miR-000-zip or miR-21-zip cells were treated with MCG. Data are mean±SD (n=4); *$p<0.05$ compared with non-treated miR-000-zip (control) cells; †$p<0.05$ compared with treated miR-000-zip cells. Differentiated THP-1 cells pre-treated with anti-TLR-4 antibody, Herbimycin, or vehicle were subsequently treated with MCG. Data are mean±SD (n=4); *$p<0.05$ compared to non-treated cells; † $p<0.05$ compared to cells treated with MCG only. The data illustrates that MCG increases phagocytosis of dead cells (bottom panel) as compared to the control (image in top panel). Macrophages in the presence of MCG have much more efficient efferocytosis than the controls. As seen in C, MCG is also associated with increased miR-21 expression, which provides evidence supporting potential applicability of MCG in a wide variety of inflammatory conditions.

Figure 17:
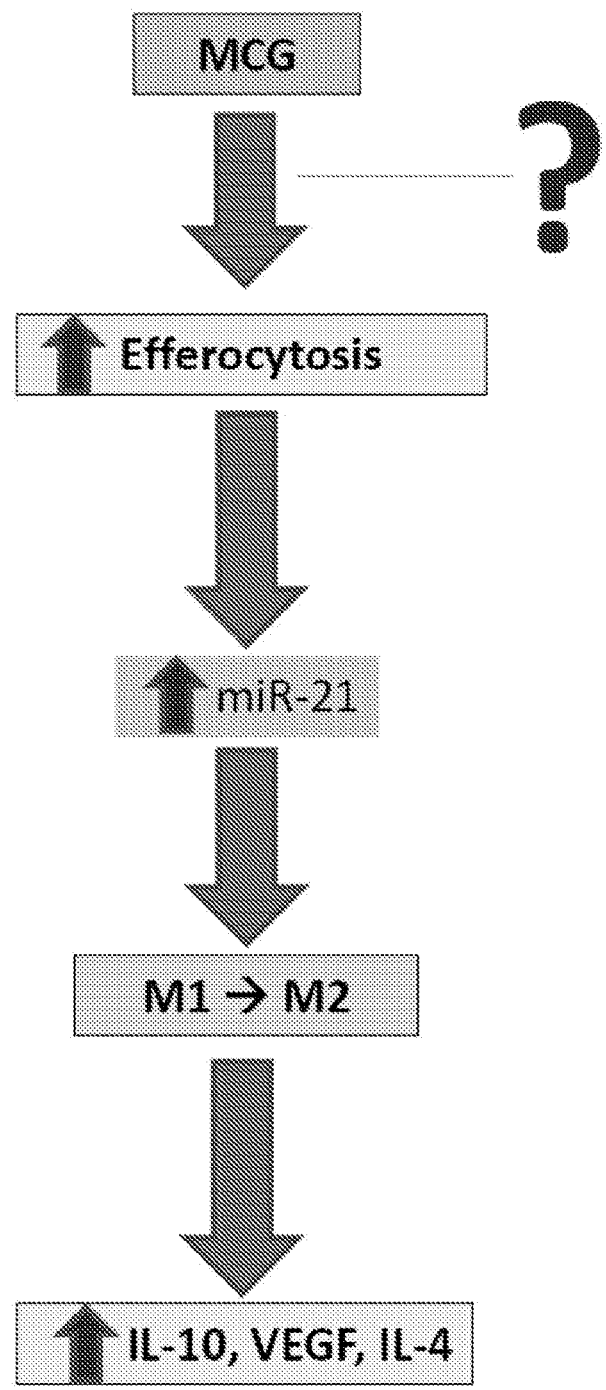
FIG. 17 illustrates a process flow for the MCG signaling process through the miR-21 pathway.

The data compares effect of MCG in IL-10 production when miR-21 is silenced (miR-21-zip). The data indicates that the activity of MCG is through a miR-21-dependent pathway. When miR-21 was silenced, there was a marked decrease in IL-10. The slight increase over the control in the silenced test is attributed to only achieving a partial silencing of miR-21 (80-90% silenced). Thus, as shown in FIG. 17, MCG signaling is through the miR-21 pathway.

We claim:

1. A method of treating an inflammatory condition comprising a chronic or ischemic site of inflammation in a patient suffering from said inflammatory condition, said method comprising:
    topically applying or injecting, for a therapeutically effective period of time, a therapeutically effective amount of a modified collagen gel composition to said site of inflammation,
    wherein said modified collagen is a hydrolyzed bovine collagen, wherein said modified collagen gel comprises a plurality of proteins comprising Hemoglobin subunit beta, Carbonic anhydrase 2, Collagen alpha-1 (1) chain, Hemoglobin subunit alpha, Peroxire doxin-2, Alpha-1-antiproteinase, Serpin A3-7, Collagen alpha-1(III) chain, Collagen alpha-2(I) chain, Serpin A3-3, Actin, and aortic smooth muscle, and reduces said inflammatory condition in said patient.

2. The method of claim 1, wherein said site of inflammation is a site of dermal inflammation.

3. The method of claim 1, wherein said reduction of inflammation comprises action by said collagen gel to up-regulate anti-inflammatory cytokines of said patient to thereby reduce inflammation in said inflammatory condition of said patient.

4. The method of claim 1, wherein said modified collagen gel increases the ratio of the patient's collagen type I to collagen type III at said site of inflammation.

5. The method of claim 1, wherein said modified collagen gel composition comprises a dispersion of about 52% by weight hydrolyzed bovine collagen, dispersed in an aqueous matrix comprising water and glycerine.

6. The method of claim 1, wherein said modified collagen gel composition comprises from about 25 to about 75%, by weight modified collagen, based upon the total weight of the composition taken as 100% by weight.

7. The method of claim 1, said modified collagen gel comprises modified collagen of long and short polypeptides dispersed in an aqueous matrix.

8. The method of claim 1, wherein said modified collagen gel comprises from about 25 to about 75% by weight modified collagen dispersed in an aqueous matrix, based upon the total weight of the gel composition taken as 100% by weight.

* * * * *